US012558567B2

(12) United States Patent
Díaz Arias

(10) Patent No.: US 12,558,567 B2
(45) Date of Patent: Feb. 24, 2026

(54) EQUIPMENT FOR DESTRUCTION OF CORONAVIRUSES BY MEANS OF COMPLEMENTARY RADIATION

(71) Applicant: Herman Díaz Arias, Atizapán de Zaragoza (MX)

(72) Inventor: Herman Díaz Arias, Atizapán de Zaragoza (MX)

( * ) Notice: Subject to any disclaimer, the term of this patent is extended or adjusted under 35 U.S.C. 154(b) by 521 days.

(21) Appl. No.: 17/996,624

(22) PCT Filed: Apr. 20, 2021

(86) PCT No.: PCT/IB2021/053267
§ 371 (c)(1),
(2) Date: Oct. 20, 2022

(87) PCT Pub. No.: WO2021/214668
PCT Pub. Date: Oct. 28, 2021

(65) Prior Publication Data
US 2023/0201626 A1 Jun. 29, 2023

(30) Foreign Application Priority Data
Apr. 21, 2020 (MX) .................... MX/a/2020/004121

(51) Int. Cl.
*A61N 5/06* (2006.01)

(52) U.S. Cl.
CPC .... *A61N 5/0624* (2013.01); *A61N 2005/0626* (2013.01); *A61N 2005/0632* (2013.01); *A61N 2005/0658* (2013.01)

(58) Field of Classification Search
CPC .......... A61N 5/0624; A61N 2005/0626; A61N 2005/0632; A61N 2005/0658;
(Continued)

(56) References Cited

U.S. PATENT DOCUMENTS

2002/0173833 A1 11/2002 Korman et al.
2009/0081075 A1* 3/2009 Hashiba .................... A61L 2/24
422/186
(Continued)

FOREIGN PATENT DOCUMENTS

DE 2533689 A1 2/1977
MX 2016004383 A 10/2017
(Continued)

*Primary Examiner* — Ankit D Tejani
*Assistant Examiner* — Joshua Brendon Solomon

(57) ABSTRACT

The equipment for the destruction of viruses by means of complementary radiation consists of a technology focused on weakening the fatty layer covering certain viruses, to cause the indirect destruction of them. This technology utilizes intense, modulated light radiation, the principal emitters thereof being 460-nanometers LEDs which, with the technology of the invention, emit secondary radiation in a band ranging from 400 to 460 nanometers, in order to achieve the weakening and destruction of the fatty layer that covers viruses such as SARS-CoV-2. This light radiation is complemented with ultrasound pulses that complete the destructive effect of the interior of the virus. For this purpose, technology involving emission by means of stratified quantum excitation is employed, which uses monochromatic light-emitting diodes to achieve very-high-intensity polychromatic emissions highly controllable regarding tissue penetration.

9 Claims, 14 Drawing Sheets

(58) Field of Classification Search
CPC .... A61N 2005/0642; A61N 2005/0652; A61N 2005/0662; A61B 5/00; A61B 7/00; A61B 7/02; A61B 18/18; A61L 2/02; A61L 2/025; A61L 2/08; A61M 1/36; A61M 37/00
See application file for complete search history.

(56) References Cited

U.S. PATENT DOCUMENTS

| | | | |
|---|---|---|---|
| 2009/0171422 A1* | 7/2009 | Hillis | A61N 5/0613 607/88 |
| 2010/0082019 A1 | 4/2010 | Neev | |
| 2011/0125078 A1* | 5/2011 | Denison | A61N 5/0622 604/20 |
| 2014/0276247 A1 | 9/2014 | Hall et al. | |
| 2015/0165238 A1 | 6/2015 | Slayton et al. | |
| 2015/0217142 A1 | 8/2015 | Schafer | |
| 2017/0156597 A1* | 6/2017 | Whitehead | A61B 5/01 |
| 2018/0036554 A1* | 2/2018 | Krespi | A61N 5/0603 |
| 2018/0078696 A1* | 3/2018 | Abedin | A61K 35/17 |
| 2018/0169279 A1* | 6/2018 | Randers-Pehrson | A61L 2/0047 |
| 2019/0054172 A1 | 2/2019 | Gavalda Santapau et al. | |
| 2019/0134422 A1 | 5/2019 | Schafer et al. | |
| 2024/0207475 A1* | 6/2024 | Kaler | A61L 9/20 |

FOREIGN PATENT DOCUMENTS

| | | | |
|---|---|---|---|
| RU | 2433785 C1 | 11/2011 | |
| WO | WO-2021195003 A1 * | 9/2021 | A61L 2/10 |

* cited by examiner

EQUIPMENT FOR DESTRUCTION OF CORONAVIRUSES BY MEANS OF COMPLEMENTARY RADIATION

FIELD OF INVENTION

The present invention is developed in the field of Biochemistry, Medicine, Optoelectronics, and Electronics.

BACKGROUND OF THE INVENTION

Parallel to the efforts that have been made to combat viral and bacterial infections by purely chemical means, as well as by genetic and biological manipulation, a significant effort has been made to develop, both theoretically and practically, devices based on the radiation of electromagnetic and mechanical waves. Basically, these efforts have been focused on the destruction of the core of viruses. So far, it has not been possible to develop an optimal solution to combat viral epidemics by completely physical means. It is known that ionizing ultraviolet radiation can destroy almost all viruses: however, this radiation produces considerable damage to surrounding tissues, which makes its practical use in patients impossible. Ultra-high-frequency waves in the order of 60 Giga Hertz have been seen to allow the modification and, in some cases, the destruction of the core of certain viruses, although this type of treatment has not yet been perfected for general use. One of the main problems that this type of therapy has had to face is the poor penetration of radiation into the body, so it has had to resort to extracorporeal circulation techniques, extracting the patient's blood and directing it towards a chamber where the blood is irradiated and later re-entered into the patient's body. These dialysis-type techniques have the problem that they can only attack viruses in the bloodstream, but in cases such as the Coronavirus SARS-CoV-2, there is a high concentration of pathogens in the lungs, heart and kidneys, places not normally accessible with this type of radiation technology currently in development.

In cases such as the Coronavirus SARS-CoV-2, there are still no medications to combat it and the development of vaccines to prevent it takes a long time. To have a non-invasive treatment that does not depend on drugs or biological solutions specifically designed is an instrument of enormous value worldwide. It is also important to note that many viruses, especially those based on RNA, can mutate, which eventually leads to the need for continued development of vaccines and medicines.

SUMMARY OF THE INVENTION

The technology object of the present invention consists of the use of a mixture of electromagnetic radiation, particularly in the range of 400 to 460 nanometers (blue light) and ultrasonic and hypersonic mechanical waves in order to attack the fat or lipid cover that surrounds certain viruses such as the SARS-CoV-2 Coronavirus and thus leave the core of the virus susceptible to being destroyed. This is a substantial difference compared to other non-invasive methods that have been developed, since the other processes directly attack the core while our technology concentrates on destroying the virus using an indirect strategy focusing on the destruction of the fatty layer that surrounds it. To apply this technology to patients, we use a device that emits pulses of high energy light in a specific range of wavelengths from 460 to 400 nanometers. This wavelength has a disruptive effect on fats and makes it go deep into the tissues. reaching the organs where the action of the viruses is more important. We use very narrow pulses in a PWM type arrangement where the valley-peak relationship allows us a great penetration without the application of an excessive amount of energy. Likewise, this technology allows combining light of different wavelengths directed towards specific areas of the patient according to a preprogrammed distribution pattern both in pulse intensity, duration, and repetition frequency. This is due to the fact that another range of wavelengths between 650 and 950) nanometers are used in this therapy to complement the disruptive actions of blue light (400 to 460 nanometers) since irradiation with light or photon pulses in the range of 950 to 650 nanometers produces an increase in ATP (adenosine triphosphate) levels, which is an element that provides energy to the cells and participates positively in their strengthening and recovery.

The equipment for the destruction of viruses by means of complementary radiation emulates the process of washing hands that has proven to be highly effective in controlling the proliferation of the SAR-CoV-2 Coronavirus, since this procedure weakens the lipid layer of the coronavirus, making it soluble in water through saponification. Once this is done, the pressures and tensions of mechanical nature allow the destruction of the virus nucleus. Our system consists of weakening the lipid layer through the action of electromagnetic waves, specifically light energy in the vicinity of 460 nanometer wavelength, to then attack the virus with ultrasound waves in order to finish the destruction of the virus once it has lost its fatty protection. This action is also complemented by subsequent irradiation with light energy of a larger wavelength to generate collateral effects that contribute to the structural destruction of the virus and cell strengthening.

The modular nature of this system allows the design of specially planned equipment for the treatment of patients in remarkably diverse conditions and situations and at various stages of the disease: chairs, tables and radiation chambers can be made to provide treatment to patients automated or manually with a personalized time schedule.

Once the fat cover is destroyed, the application of focused ultrasonic waves allows rapid destruction and disintegration of the virus and can be used not only in dialysis-type devices (with extracorporeal circulation) but also with direct external application to the organs of interest. Likewise, the irradiation heads can be used to irradiate equipment and accessories such as masks, gowns, and instruments to help limit the spread of the virus.

For the generation of the energy that will weaken the lipid cover of the virus, we use an unconventional technology for the excitation of light-emitting diodes. This technology uses a quantum treatment radically different from the traditional treatment of the generation of light energy through LEDs, which allows the generation of remarkably high energy levels in extremely short pulses accompanied by the emission of secondary radiation in harmonic wavelengths. This technology is based on a proprietary LED and laser excitation technology known as quantum layered excitation of light-emitting diodes, which allows the highest levels using light-emitting diodes and a multichromatic emission with monochromatic diode crystals. This enables broad control of irradiation penetration, as well as of the range of wavelengths that make up each pulse emitted during treatment. Thus, the technology at hand is designed for implementation around light-emitting diode layered quantum excitation technology emitter heads but modifying the way in which the maximum and minimum levels of radiation are controlled and modulated.

DETAILED DESCRIPTION OF THE INVENTION

Traditional methods for fighting diseases caused by viruses are mainly based on the development of biochemical devices, vaccines, and drugs specifically designed to combat a certain virus, rather than with a generic approach. On the other hand, there is a current trend to develop technologies that allow the destruction of viruses in a more generic way. So far, these efforts have focused primarily on the destruction of the nucleus and the genetic material of the virus. The equipment for the destruction of viruses by means of complementary radiation, i.e., the object of the present invention, has a completely different approach and is based on a technology that allows the destruction of the fat or lipid layer that surrounds a wide variety of viruses, some of which are among the most lethal, such as SARS-CoV-2. This technology that concerns us, allows the saponification of fats or lipids at a distance, that is, it dissolves fats just as a soap does. In fact, one of the most accepted methods worldwide to prevent the spread of the SARS-virus CoV-2 consists of washing hands with soap for several seconds in order to destroy the fatty layer that covers the virus core, leaving it vulnerable to the pressure and mechanical stress that expose and destroy the genetic material in the virus core.

Figure 1:
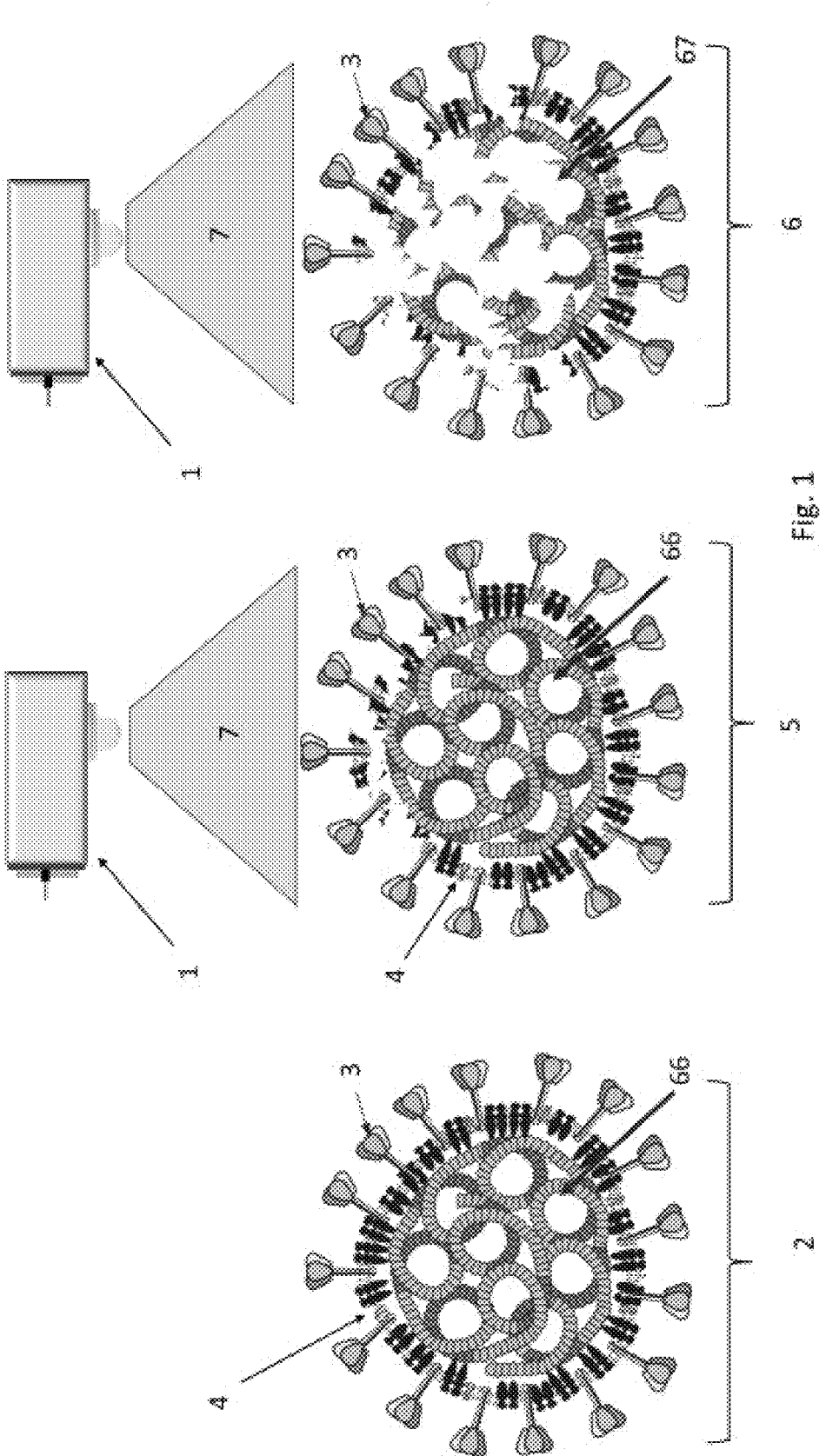
FIG. 1 shows a coronavirus in various stages of disintegration by the photonic irradiation process.

FIG. 1 shows a coronavirus (2) with has a series of structural protein projections (3), a fatty cover (4) and a nucleus with a non-segmented RNA genome (66). When exposed to intense pulses of photon radiation in the range of 390 to 480 nanometers, through the use of a photon pulse generator equipment (1) producing an intense and penetrating photon irradiation (7), this virus quickly presents a deterioration in the fat layer or lipid that surrounds it, as shown by the coronavirus with a fat cover damaged by radiation (5), which is why it begins to expose its ribonucleic acid (RNA) genetic material, leaving its nucleus vulnerable, leading to a coronavirus with a destroyed nucleus (6). In this step, the nucleus with destroyed RNA (67) is disabled in such a way that the virus can no longer continue causing damage. To reinforce the destructive action on the internal structure of the virus, we combine photo irradiation (7) with ultrasonic irradiation. This ultrasonic irradiation is also carried out in the form of high-energy pulses and using various modulation frequencies to create pressure zones based on the interference of waves which, when hitting a point, create pressure points due to the phase coincidence of the various ultrasonic pulses, that is, if one ultrasonic wave crest coincides with another, its magnitude is added while when it coincides a crest with a trough the resulting pressure effect is the subtraction of both waves.

Figure 2:
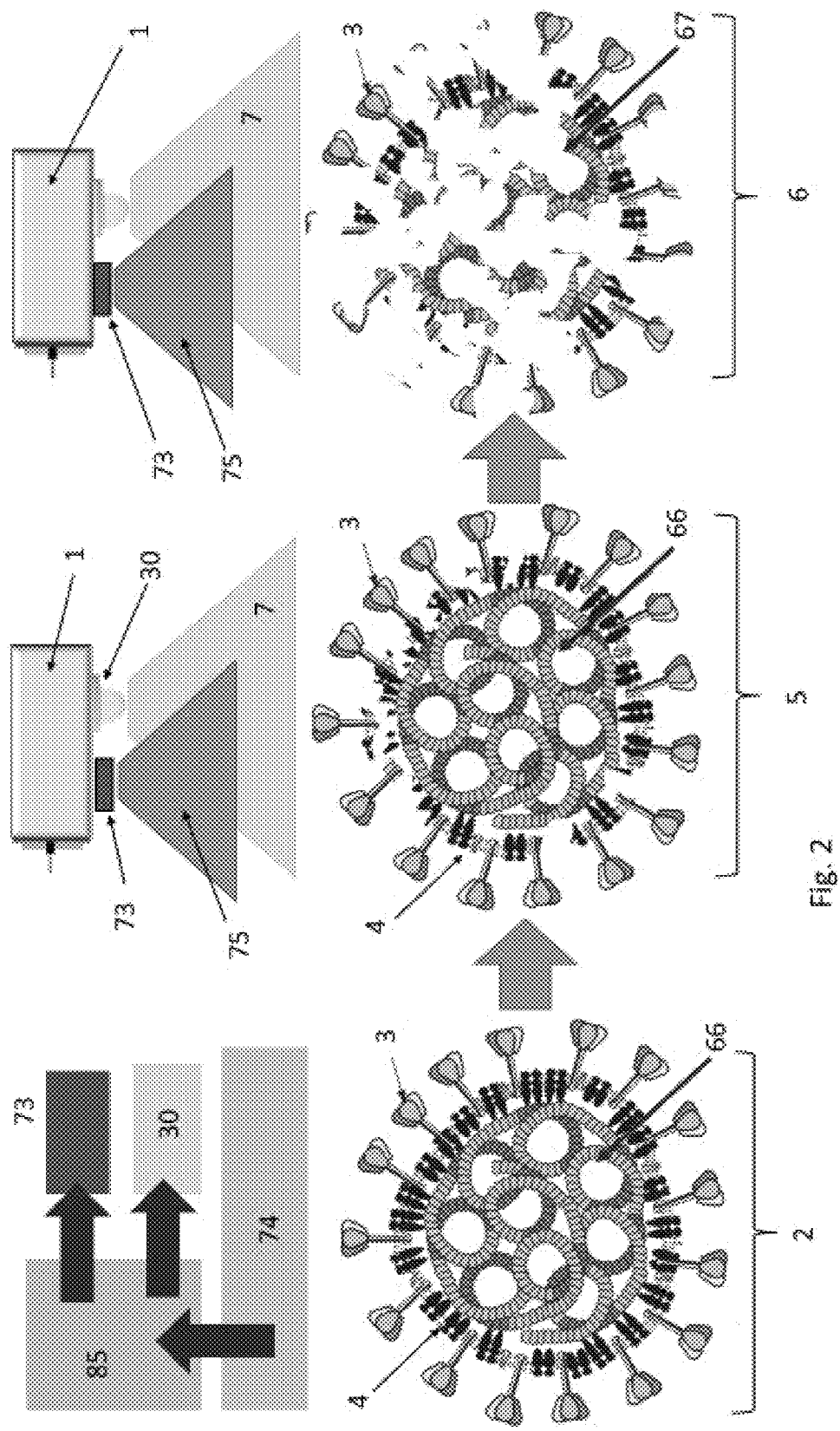
FIG. 2 shows a hybrid equipment for the destruction of viruses, with photonic heads complemented by an ultrasonic wave emission system.

The complementary action of both types of radiation, photonic and ultrasonic, act in a comparable way as washing hands with soap and water does on hands contaminated with viruses, that is, a saponifying agent is combined with an agent of mechanical force. As can be seen in FIG. 2, a modulated ultrasound emitter (73) is added to the photonic pulse generator equipment (1), which produces ultrasonic radiation (75) with high penetration into cells and tissues. The optical emission circuit (30) suitably focuses the photonic radiation (7) in such a way that the energy of both radiation sources is combined to first weaken the fatty layer surrounding the virus and subsequently destroying the structure and genetic material of the virus.

The complete radiation head is integrated into a single unit where the optical emission circuit (30) and the modulated ultrasound emitter (73) are coordinated by a central control (85), powered by a general power supply system (74).

Photon radiation can be of various wavelengths, but fundamentally we use light with a wavelength in the vicinity of 460 nanometers. This type of blue light has the property of saponifying fats: however, in order to generate the saponification of lipid cover of viruses in living tissues, it is necessary for this photonic emission to have an extraordinarily high intensity. The light we use is preferably produced by light-emitting diodes (LEDS) or by laser diodes. In both cases the intensity of light necessary to penetrate several centimeters under the skin could burn the patient: that is why the generation of remarkably high intensity light pulses is needed but they are spaced apart in time in such a way that deep irradiation can be counted on without exposing the treated area to extremely elevated levels of energy. To achieve this, we employ a method of activating light-emitting diodes completely different from the conventional method.

The general practice for the activation of light-emitting diodes, whether they are simple LEDs or laser diodes, consists of passing through them a controlled current, either constant or pulsed. In the equipment object of the present invention, we use the introduction of high-voltage carriers. energy (electrons or holes) onto an array of light emitting diodes without any limitation on current flow, and we let the carriers flow through the array until the array is about to thermally collapse, at which point the supply of carriers is completely cut off and a time is allowed for the latent temperature of the light emitting diode array to decrease based on the predetermined thermal flow, which is aided by active dissipation by means of fans and dissipation fins. Once the thermal dissipation allows it, the activation cycle is repeated, thus generating a train of very high-power light pulses, which contain wavelengths extending from the fundamental wavelength of the emitter to several tens of nanometers down. This means that if the emitting matrix has a fundamental wavelength of 460 nanometers, the emitted pulses will contain light in the range of 460 nanometers to just over 400 nanometers.

Figure 3:
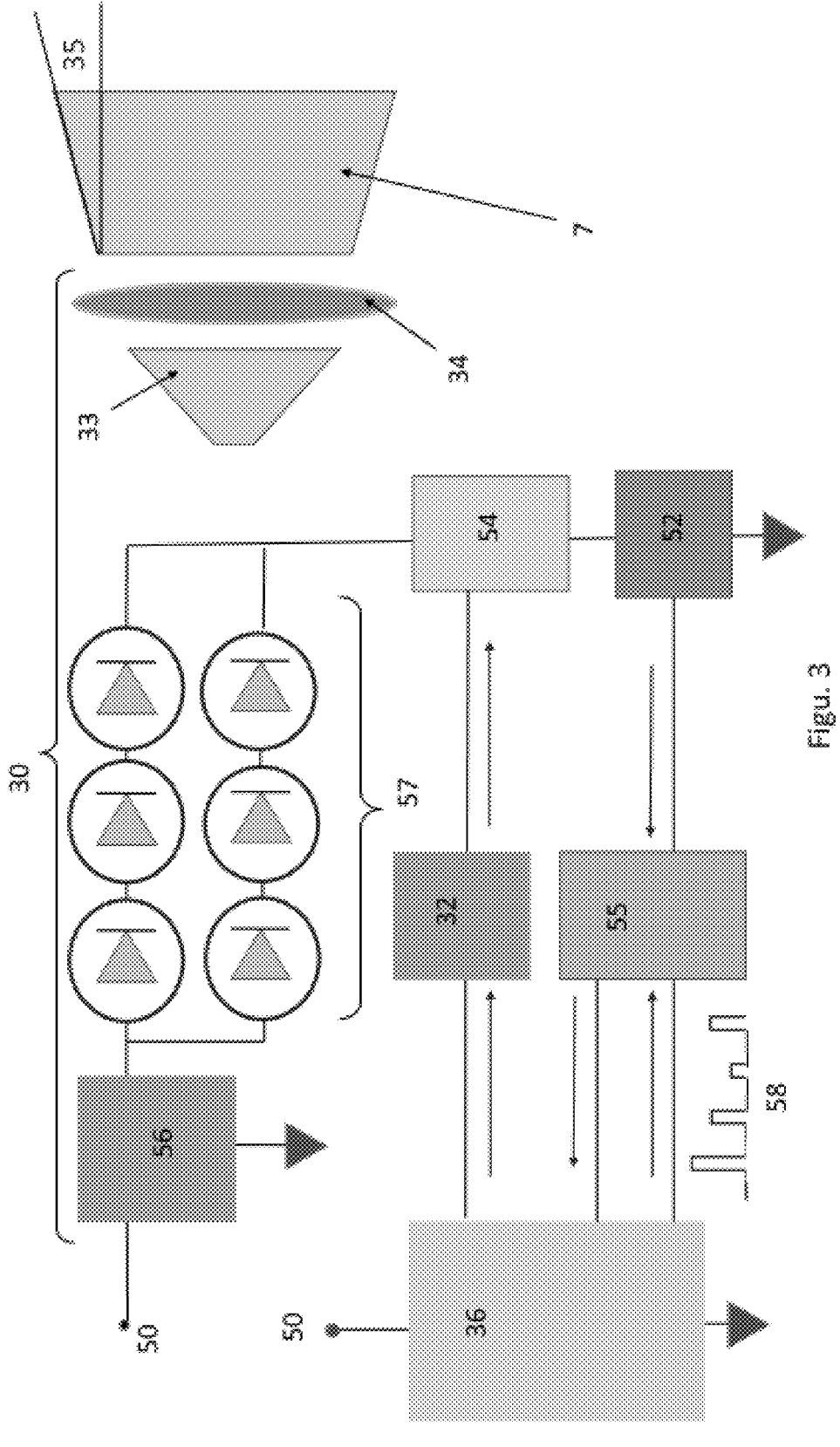
FIG. 3 shows a photon emission diagram for the destruction of viruses.

FIG. 3 shows an optical emission circuit (30). This circuit is based on the principle of stratified quantum excitation of light emitting diodes, which works by exciting the light emitting diodes with remarkably high voltage pulses (several times the nominal working voltage of the light emitting diodes), whether they are LEDs or lasers. This overexcitation causes the carriers (electrons or holes), to reach a stable energy state when crossing the diode junction. The excess energy is released through a stratified energy jump, that is, a single carrier can emit different wavelengths until it stabilizes since the amount of photon energy is established by a constant multiplied by the frequency of the emitted radiation, only the excess of the photonic emissions before achieving stability, is transformed into heat. This technology allows for remarkably elevated levels of photon energy and makes it possible for a light-emitting diode nominally designed to emit light at a certain wavelength to emit secondary radiation at shorter (higher energy) wavelengths, in addition to the basic emission.

The use of this technology also makes it possible that with a 460-nanometer light emitting diode array, a secondary radiation is emitted at 450 and 430 nanometers. We have added an OOK type modulation to this system to achieve a mechanical impact effect in addition to the photonic or luminous effect. Although the equipment for the destruction of viruses by means of complementary radiation object of the present invention can work with a photonic illumination system with conventionally activated emitters, the use of stratified quantum excitation heads of light-emitting diodes gives the perfect combination of pulses extremely narrow beams, high power, and photon emission in a controlled bandwidth range. By adding to the basic concept of stratified excitation emission an OOK type modulation and multiple selectors of lighting matrix sections, optimal illumination is achieved not of one area but of a given volume of the patient's body.

The optical emission circuit (30), as shown in FIG. 3, is formed by an array of high-power LED or laser emitters (57), which comprise a set of solid-state elements, each of them with an electrical power capacity of more than one watt but grouped in arrays of 30 or more watts per unit. Emitters with lower power capacity can be used but this would extend the time necessary for the patient to be exposed to treatment. If the array power is maintained between 30 and 150 watts, the times for each treatment can be contained within a period of 3 to 5 minutes. The light energy emitted by the array of light emitters (57) has a primary radiation pattern (33) that must be concentrated by a focusing device (34) to generate a photonic irradiation pattern (7) with a suitable scattering angle (35). The array of emitters (57) has an excitation circuit formed mainly by an electrical power supply system (50), a low impedance voltage source (56), which must have a low inductance in the range of micro-Henry's of output as well as an electrical resistance of fractions of milli ohms. This is achieved with the help of special discharge capacitors for pulse handling, the excitation or disconnection of the emitter array (57) is controlled by a high-speed solid-state switch (54) (with switching times less than two or three tens of nanoseconds). The system uses an energy estimator (52) to evaluate the amount of electrical energy that has passed through the matrix or array of emitters (57) and that will be converted into light and heat. The function of this energy estimator element is to give the integrating device and controller of pulses (55) the information necessary for it to estimate when the energy supply should be interrupted through the matrix or array of emitters (57) of LED or laser diodes. This is done in such a way that the maximum duration of a pulse at the maximum current flow capacity can be achieved without measuring the amount of thermal energy that is generated and that could cause the destruction of the emitting matrix, starting from the fact that the circuit and the thermal flow are known, which in this case is an active thermal flow assisted by fans, which gives us a theoretical value on the maximum amount of electrical energy that can flow through the matrix before that falls into a regenerative process of destruction. It should be remembered that the potential drop in each light-emitting diode depends on the temperature. Because of this, once the integrator circuit and pulse controller (55) consider that the power supply through the matrix must be cut off, it gives the emission power control (36) the information to start a process of absolute disconnection of the matrix through the high-speed solid-state switch (54). To achieve this, it is necessary that the shutdown command has sufficient electrical capacity to deal with the capacitances and parasitic elements found at the input of the activation control of the high-speed solid-state switch (54). To achieve this, a current amplifier (32) is used, so that the orders to activate or deactivate coming from the emission power control (36) arrive with enough energy to the high-speed solid-state switch (54). Although this circuit is capable of emitting the highest levels of light energy that a matrix of light-emitting diodes can provide, it also protects them from destruction by self-generated heat and also allows, having determined the maximum value of energy that can flow through the matrix of emitters, to control his energy downward, that is, it can be varied using energy levels below the maximum and can even be modulated according to a specific program. Thus, we have introduced here a way to generate photonic pulses with the ability to generate significant mechanical forces by impact, based on the proprietary technology of stratified quantum stimulation of LEDs but modifying the way in which the maximum and minimum levels of radiation are controlled based on a digital signal and an OOK-type modulation that can generate mechanical vibrations at the impact of photonic pulses. This digital control signal for optical impact (58) acts on the integrator and pulse controller (55) to achieve the duality of optical and mechanical effects.

Figure 4:
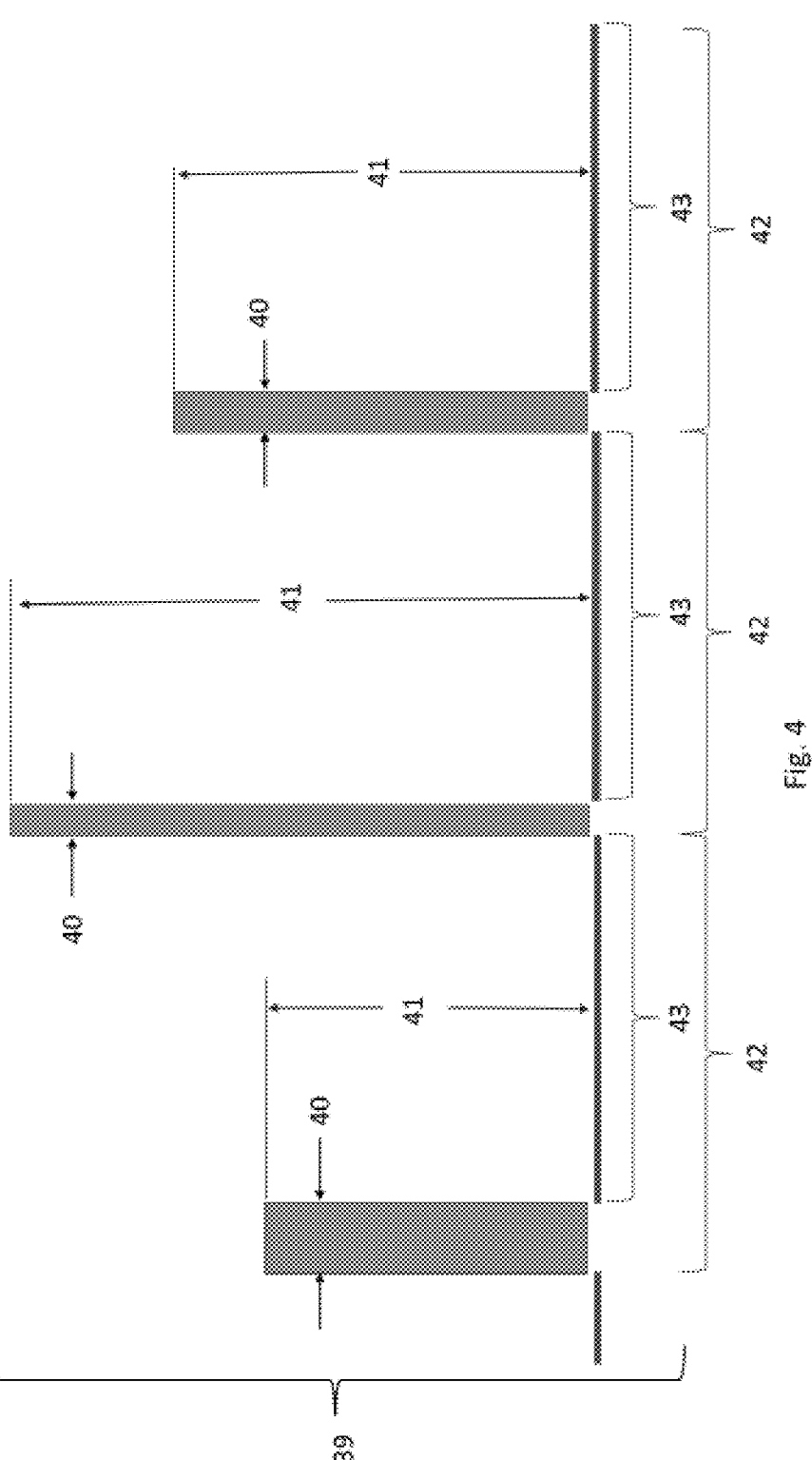
FIG. 4 shows the formation of the radiation pulse trains.
Figure 5:
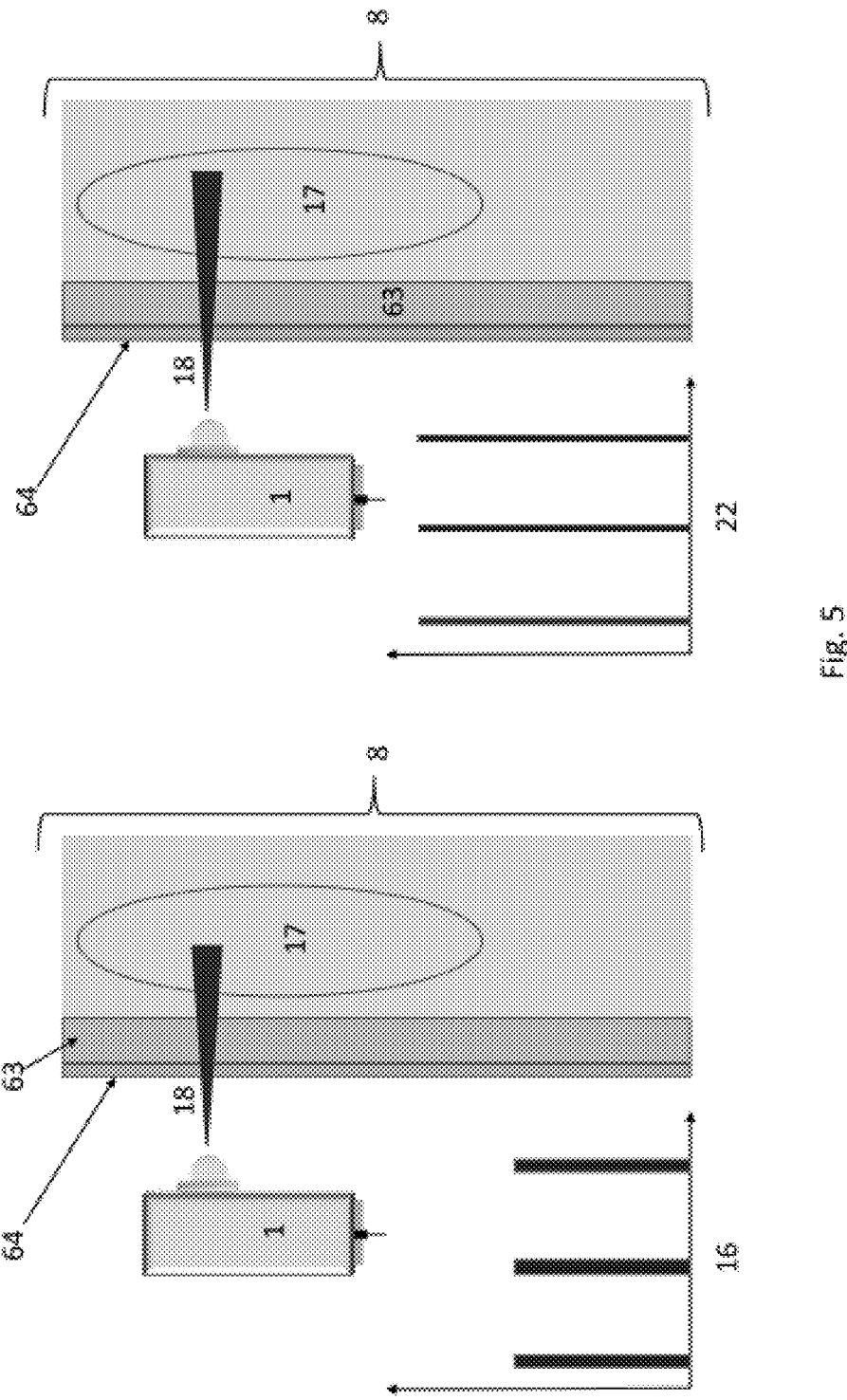
FIG. 5 shows the penetration of photon irradiation into the skin and tissues as a function of the width and intensity of the energy pulses.

The duration and intensity of each light pulse is particularly important, as is the repetition rate, that is, how many pulses are emitted per second, as well as their modulation. It is of paramount importance that the amount of energy dissipated in each cycle by the array of light-emitting diodes or array of emitters (57) does not exceed the maximum allowed by the thermal flow; as shown in FIG. 4, the optical emission circuit (30) can generate low and narrow pulses or low and wide pulses. The emission power diagram (39) shown in FIG. 4 allows to see how the emission power control (36) establishes how the photon emission will be, in such a way that the pulse width (40) and the pulse height (41) can be varied according to a predetermined emission but always taking into account the area ratio of each pulse (width by height) and the dead time between pulses (43). Over a period (42) of time that can be variable, fixed or adjustable, the modulation of the pulses and their shape is established according to the treatment and the area of treatment to be irradiated, In FIG. 5, a section of the patient (8) is schematically shown: the radiation beam (18) must pass through the skin (64) and the muscle (63) to reach the target (17). If the pattern of pulses is a pattern of wide energy pulses (16), they will not have much penetration since these are not so intense: however, narrow energy pulses (22) with greater specific intensity (joules×microsecond) can have a greater penetration within the body. In this way it is possible to reach and treat internal organs such as the lungs or the kidneys without burning the skin (64) of the patient (8): the type of treatment, the organ to be irradiated or the area subject to therapy determine the programming of the pulse train.

Figure 6:
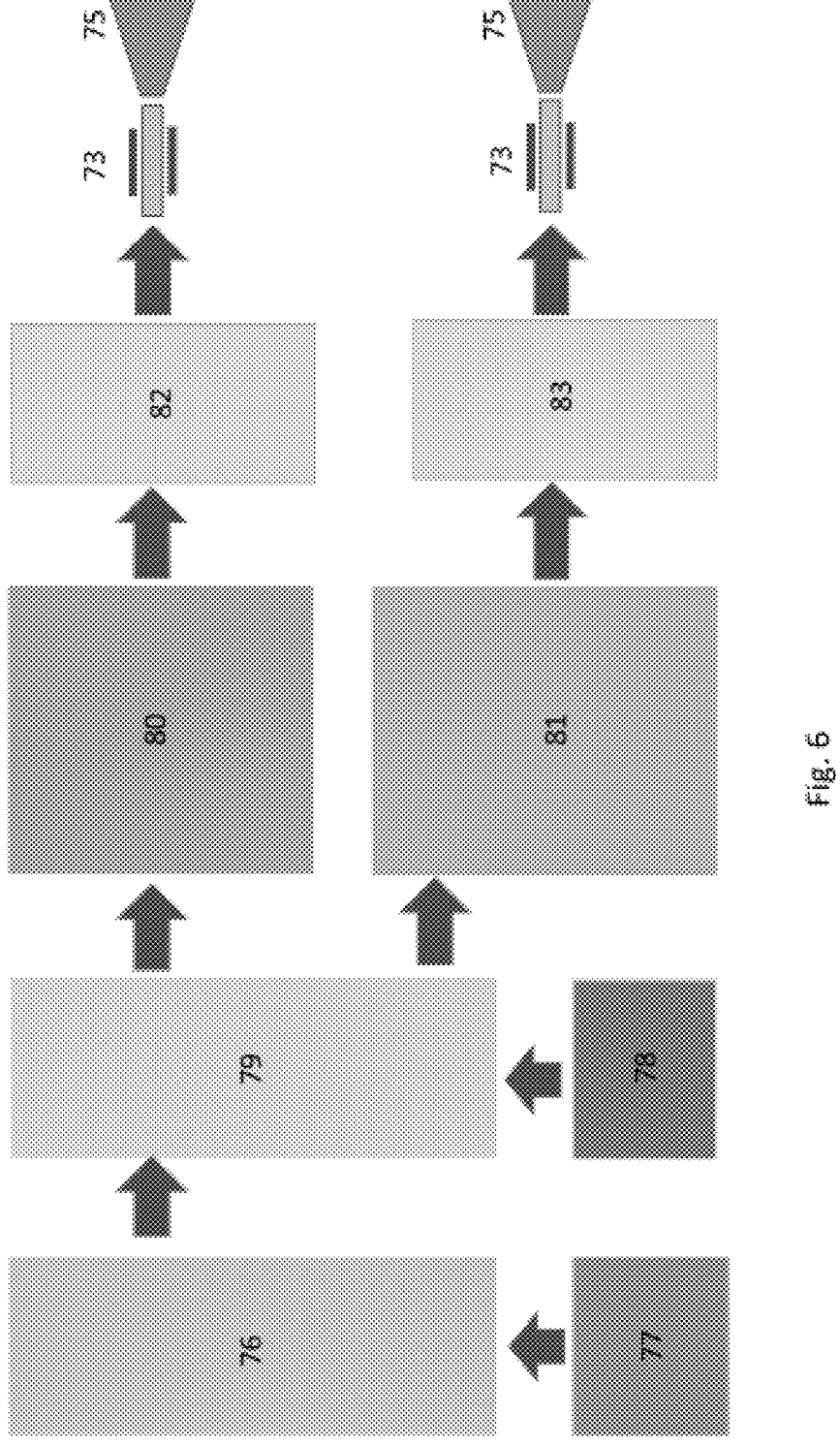
FIG. 6 shows a block diagram of the ultrasonic wave generation system with phase interaction.

Due to the technology we use to generate the photonic pulse trains, these can generate mechanical force. In fact, if the emitter is pointed towards the ear, the low frequency modulation can be heard, although no sound has been emitted, that perception of sound results from the impact of photonic shock waves so intense that it generates pressure in the impact areas. This allows us in certain cases to destroy the virus exclusively with the use of light or photon energy, since the saponification effect is achieved with light radiation but also the mechanical stress on the virus can be exerted by the pulse trains generated by the circuit described in FIG. 3. However, to reinforce the mechanical action of pressure and friction on the virus, we use ultrasonic emitters as shown in FIG. 6. The modulated ultrasound emitter (73) is arranged in pairs, both generate ultrasonic radiation (75) that is projected towards the area of the patient to be treated. Although the modulated ultrasound emitters (73) can act individually, their effectiveness is increased when acting together with other ultrasonic emitters since, in this way, interference patterns can be created that allow the generation of high-pressure zones at predetermined depths and even sweep an entire zone with pressure waves. To achieve this, we use a main resonance oscillator (76 controlled by a high frequency modulator (77) in such a way that the output of the main resonance oscillator (76) is connected to a frequency and phase modulated generator (79), which in turn is controlled by a low-frequency modulator (78). This arrangement allows the generation of two ultrasonic pulse trains that vary their oscillation frequency slightly around a base frequency in the manner of an FSK system. In addition to these pulse trains being modulated in OOK using low frequency signals, these two phase and amplitude modulated signals are connected to a primary voltage booster (80) and a secondary voltage booster (81) that give a high voltage level to the signal in order to communicate more energy to the transducers that form each of the modulated sound emitters (73). The primary and secondary impedance couplers (82) and (83) allow the maximum transfer of energy to the transducers.

Figure 7:
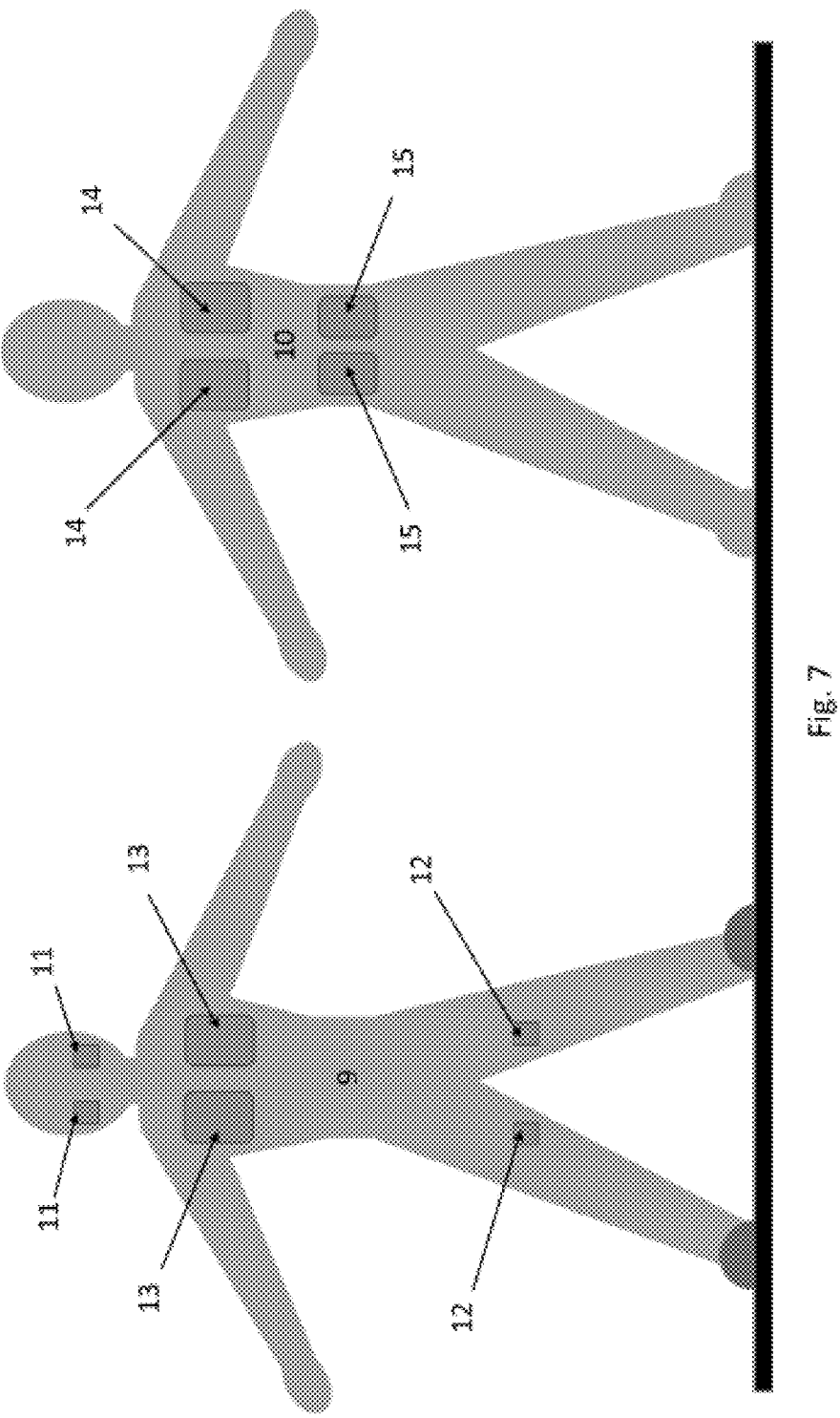
FIG. 7 shows the areas of application of both frontal and dorsal irradiation treatment.
Figure 9:
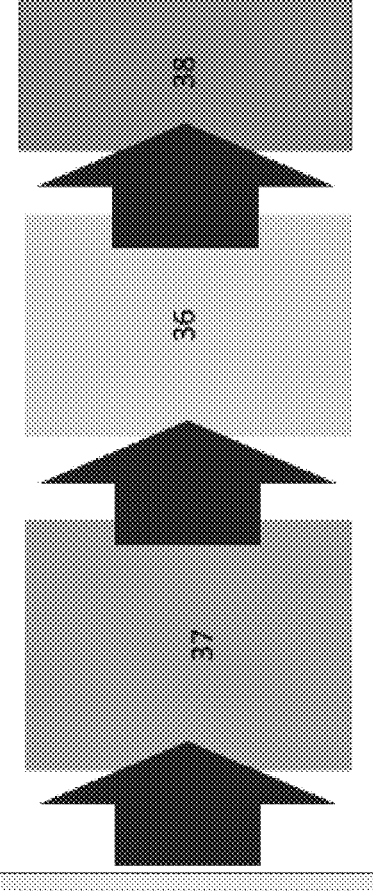
FIG. 9 shows an irradiation system with automatic positioning.
Figure 9:
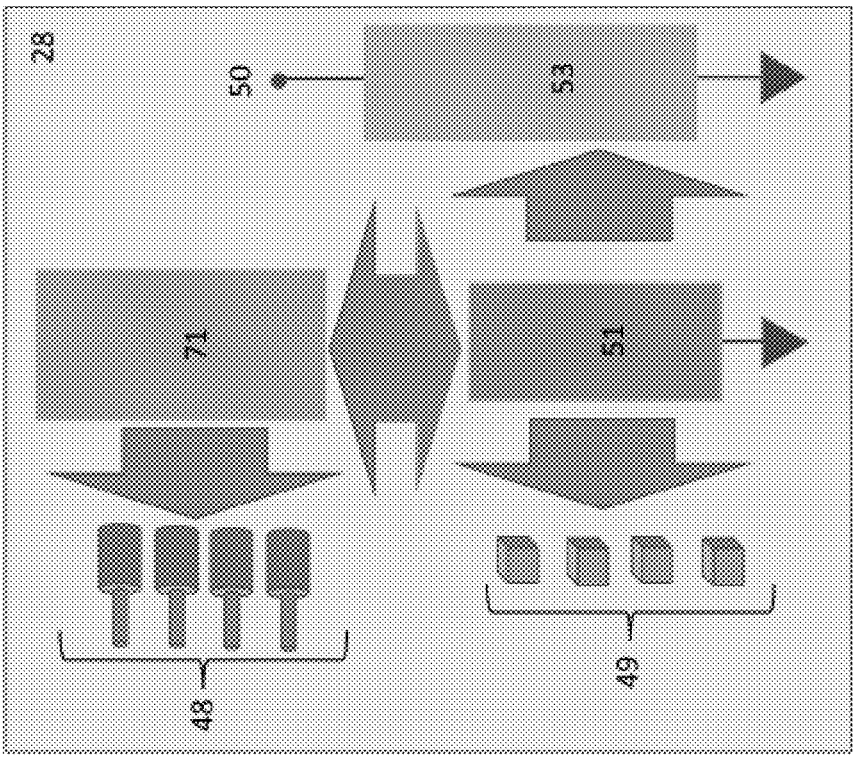

Depending on the area of the patient to be treated, a greater or lesser penetration of photon irradiation (7) and ultrasonic radiation (75) will be required. In fact, the treatment of the femoral region shown in FIG. 7 as an area of femoral treatment (12) requires little penetration, as does the facial treatment area (11). These areas are outstanding because important arteries and veins pass through them, almost the entire bloodstream passes in a time not exceeding 5 minutes. However, this only allows to combat viruses that travel in the blood. FIG. 7 shows a front view (9) of the patient and a rear view (10) of the patient where the main irradiation areas are indicated to combat viral diseases, such as the renal treatment areas (15), the frontal lung treatment areas (13), and the posterior lung treatment areas (14). These last two have the problem that the ribs intersect placed between the irradiation heads and the lungs, so a device has been designed that can move the heads avoiding the ribs, that is, it only allows the radiation of the intercostal areas. The control of this device can be seen in FIG. 9, here a group of positioning servomotors (48) allow the vertical, horizontal, and rotational movement of the heads based on the information that a set of ultrasonic transducers (49) receive in order to locate and avoid the ribs when treating the lung area, doing this automatically. These ultrasonic transducers (49) are low-power units, as opposed to the high-power units or modulated ultrasound emitters (73) referred to above. In this case the objective is to automatically position the ultrasound emitter module radiation (38), which operates under a general central control (37) and a power emission control (36). A servomotor control (71) allows positioning the radiation emitting module (38) in the best position and angle to carry out the irradiation, operating based on the information that an ultrasonic control (51) provides based on the sodar-type action of ultrasonic transducers (49). All this is coordinated by a central navigation and positioning control (53) fed by a power system (50). This assembly constitutes the automatic navigation system (28), especially useful for pulmonary treatment and it reduces the risks of infection of the operators due to proximity and contact with the patient.

Irradiation can be performed with the patient lying down or preferably sitting.

Figure 8:
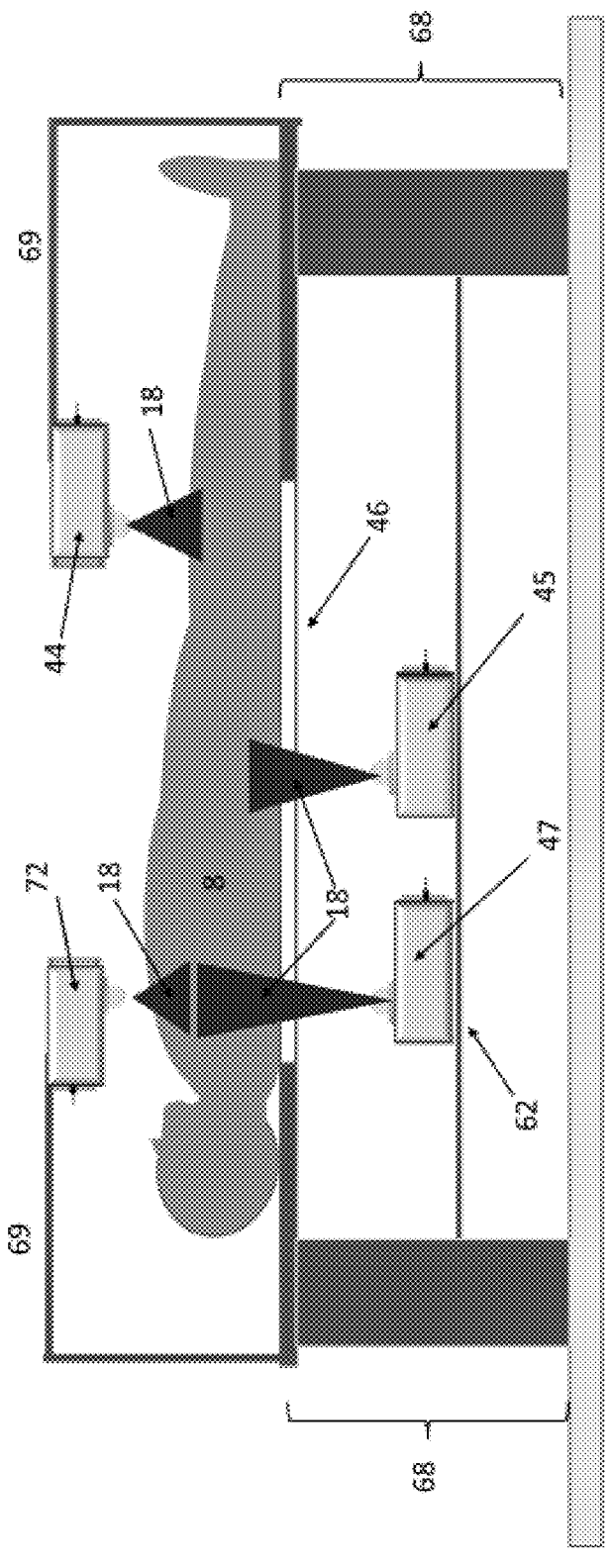
FIG. 8 shows a multipoint treatment bed.

For this, as shown in FIG. 8, a treatment table (68) is used, where the patient (8) can be placed resting upwards or downwards. A radiation transparent window (46) allows the radiation beams (18) to reach the patient (8), in this case, a modular femoral emitter set (44), a modular renal emitter set (45), a modular pulmonary emitting equipment (47) and a frontal pulmonary emitting equipment (72). Support arms (69) allow the heads or emitting equipment to be properly positioned in such a way that the radiation beam reaches the required areas. An alternative is to use a simple bed placing only headrests in the upper part: this allows half of the headrests to be used but makes it necessary for the patient (8), once he has received the frontal treatment, to turn around to receive the corresponding dorsal treatment and this doubles the total time for total treatment required for each patient.

The irradiation heads can be easily integrated into various treatment equipment aimed at treating patients at very different stages of the evolution of their condition. Although the irradiation heads and devices can be used manually to irradiate each of the areas where the virus is concentrated, these heads can also be integrated into devices such as the chair shown in FIG. 10, which is an assembly for the treatment of patients with diseases such as Covid 19 in its early stages.

Figure 10:
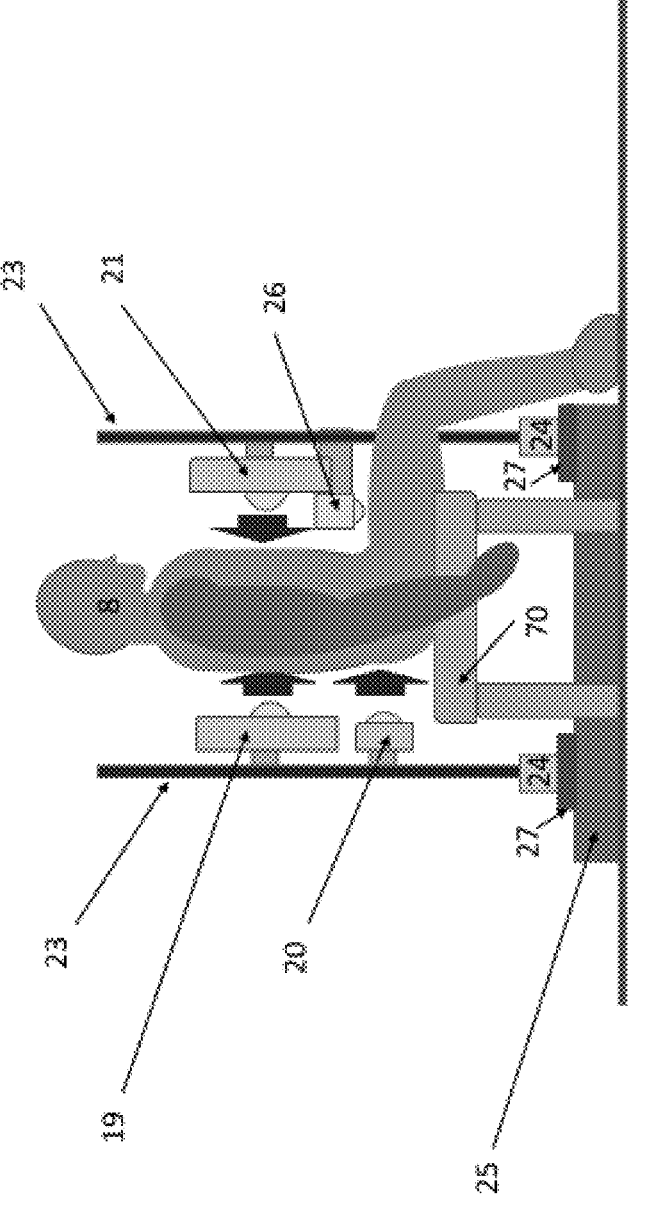
FIG. 10 shows a machine for the administration of treatments for seated patients.
Figure 11:
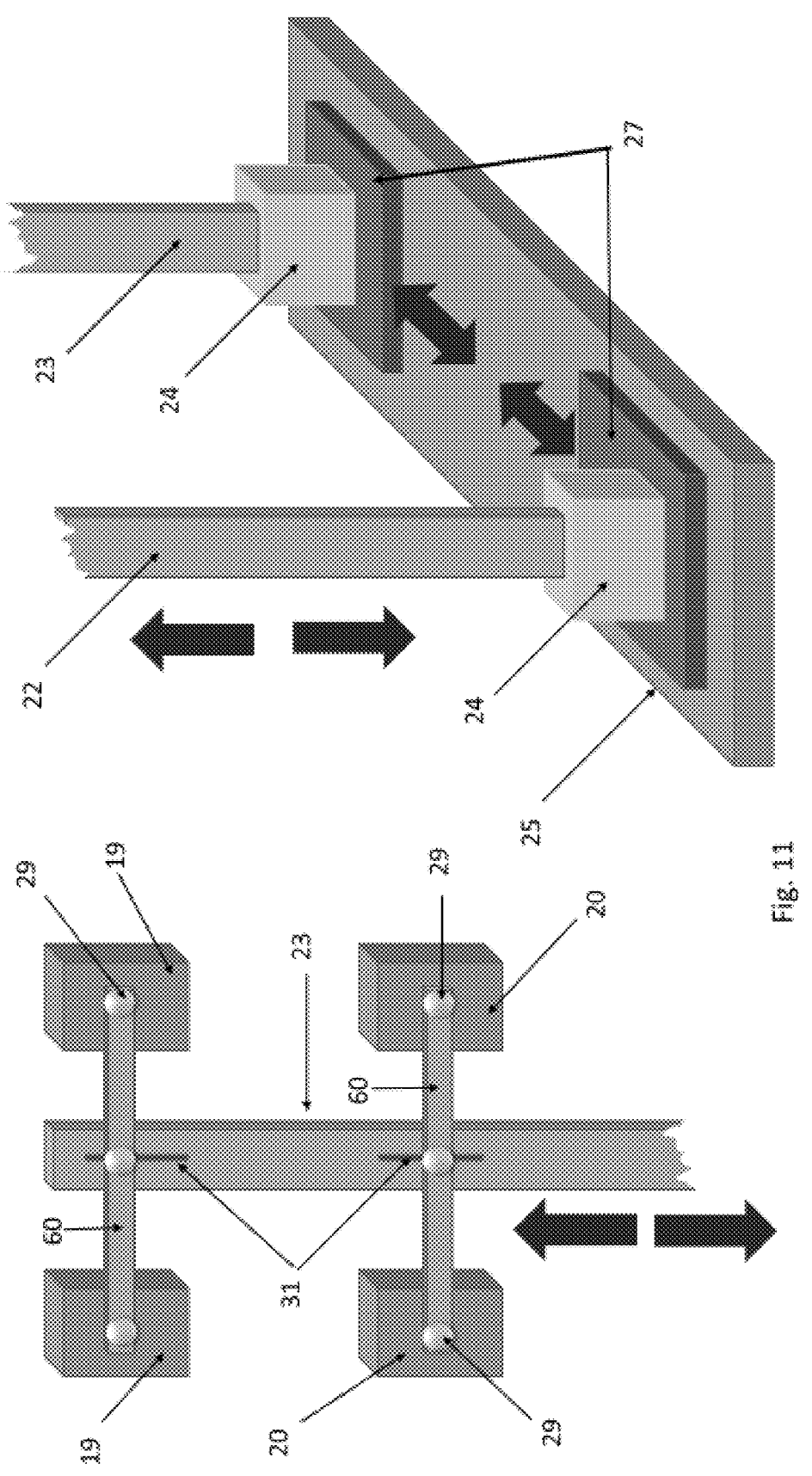
FIG. 11 shows a mechanical support structure for the radiation emitters.

The assembly shown in FIG. 10 is an assembly in which the patient sits on a bench and the equipment administers the required treatment automatically and looking for the best irradiation patterns. The patient is placed on a seat (70) and some dorsal pulmonary emitters (19), renal emitters (20), and frontal pulmonary emitters (21) give simultaneous and automatic irradiation both to the three main regions where the viruses are concentrated and to the femoral area through the femoral radiation directors (26). A pair of supports (23) that come out of vertical guides (24), secured to a general base (25) by means of a sliding base (27), allow the horizontal and rotating vertical movement of the heads for their better positioning: the renal and pulmonary heads and emitters are placed in pairs to direct the irradiation beam in the best possible way. In FIG. 11, it can be seen how the dorsal, pulmonary, and renal emitters (19), (20) are mounted by means of fixing elements (29) to positioning arms (60) that allow them to move vertically through the sliding guides (31) on the supports (23).

Figure 12:
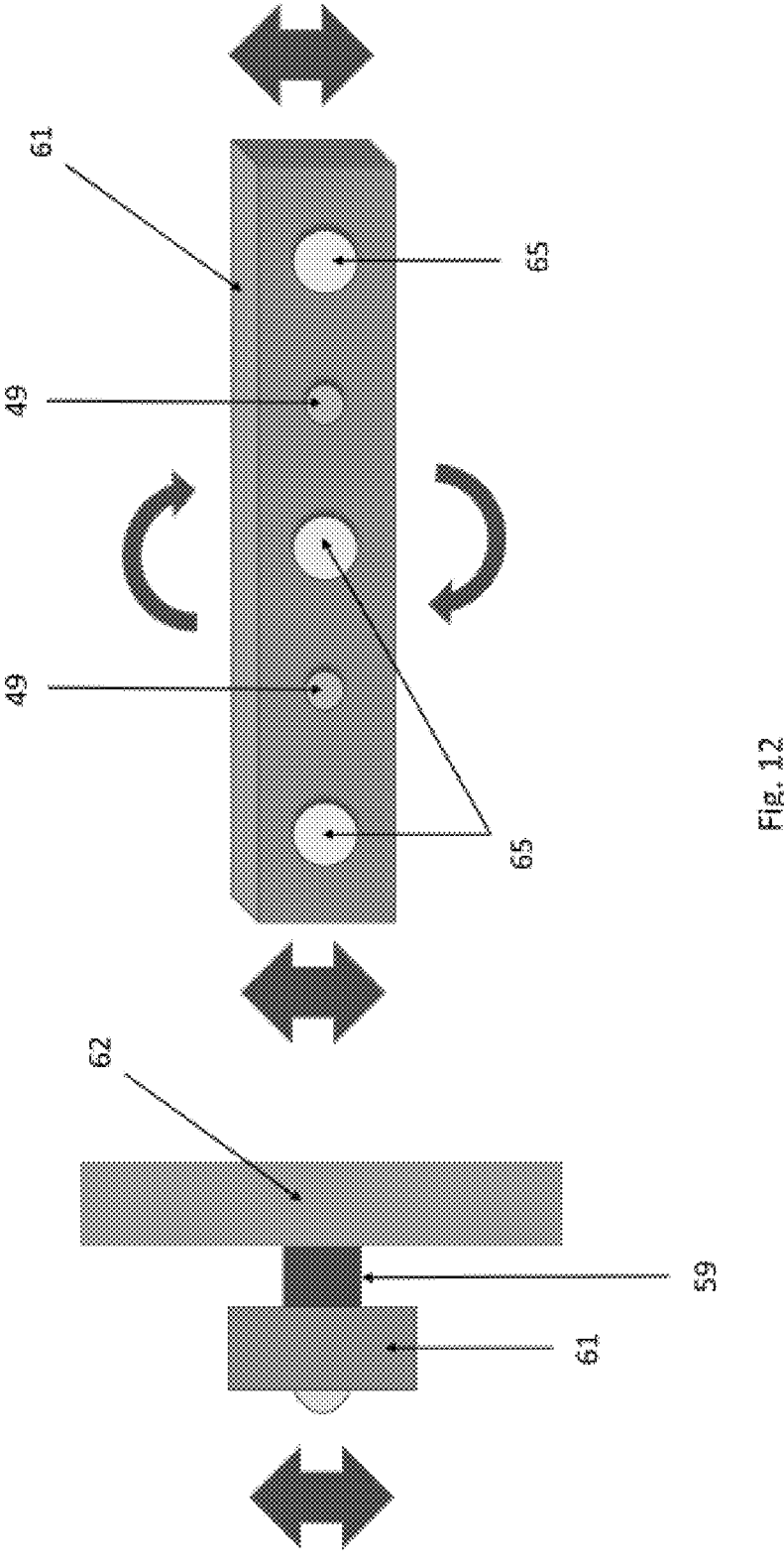
FIG. 12 shows a module with light and ultrasonic emitters.
Figure 13:
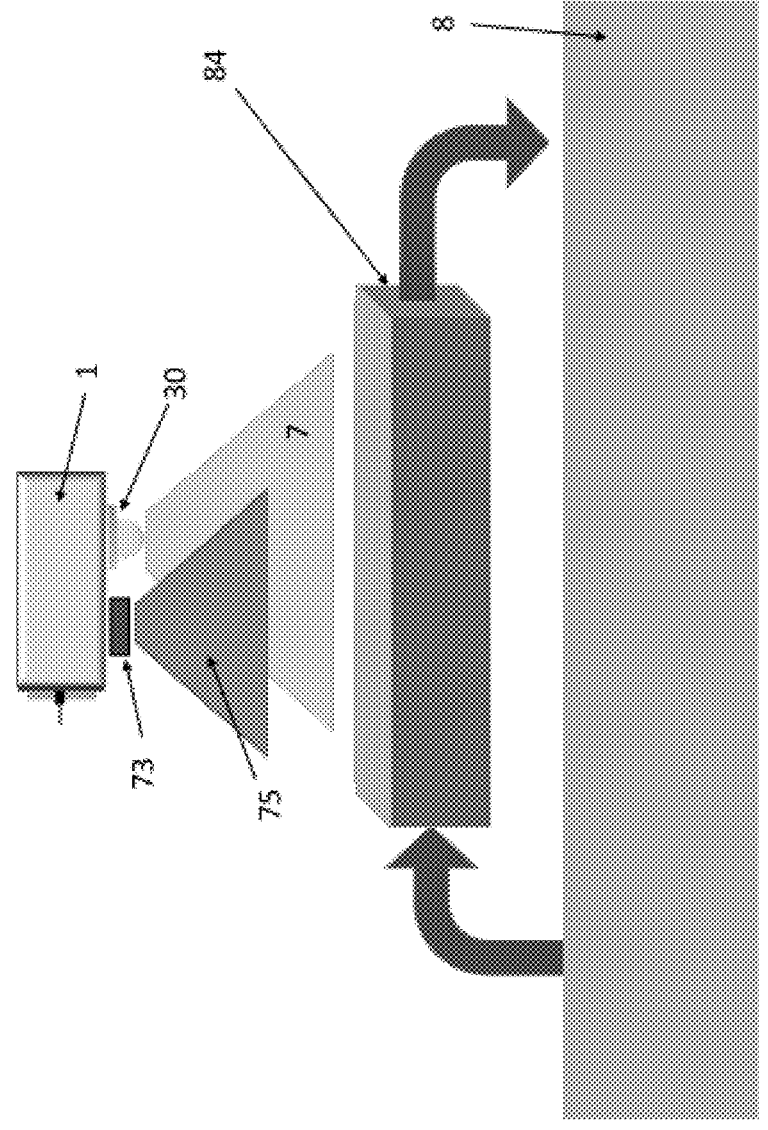
FIG. 13 shows an extracorporeal blood irradiation system.

The modularity of this system allows the construction of heads with only photonic emitters capable of emitting various wavelengths but manual and portable, mixed heads with photonic and ultrasonic emitters for irradiation also of a manual nature, modular heads equipped with photonic and ultrasonic irradiation emitters in addition to having ultrasonic transducers that work as transceivers integrated into an automatic navigation and positioning system to be integrated into automatic treatment machines. Given the capacity of the mixed irradiation to destroy viruses, the heads can also be used in sterilization stations to treat accessories and utensils such as masks, gloves, clothing for medical personnel and in general utensils that may be subject to viral contamination. FIG. 12 shows a modular radiation emitting equipment (61), mounted on an equipment support (62) by means of a modular support (59), equipped with several modular photonic emitters (65) and ultrasonic transducers (49). These heads are automatically positioned by motors or servomotors that allow them to rotate and move in various directions to achieve automatic positioning for the most correct irradiation in the required areas. Although the equipment object of the present invention is mainly focused on treatment directly on the patient's body, it can also be applied in dialysis-type treatments where the patient's blood is diverted to an external circuit to pass it through an extracorporeal irradiation chamber and then return it to the patient's body (8), FIG. 13 shows this type of application where an extracorporeal irradiation chamber (84) is used to directly irradiate the blood by means of ultrasonic radiation (75) and photonic irradiation (7) where a photonic pulse generator equipment (1), equipped with its optical emission circuit (30), is complemented by the installation of a modulated ultrasound emitter (73). Thus, there is an alternative means for the irradiation of the patient's blood when required.

Figure 14:
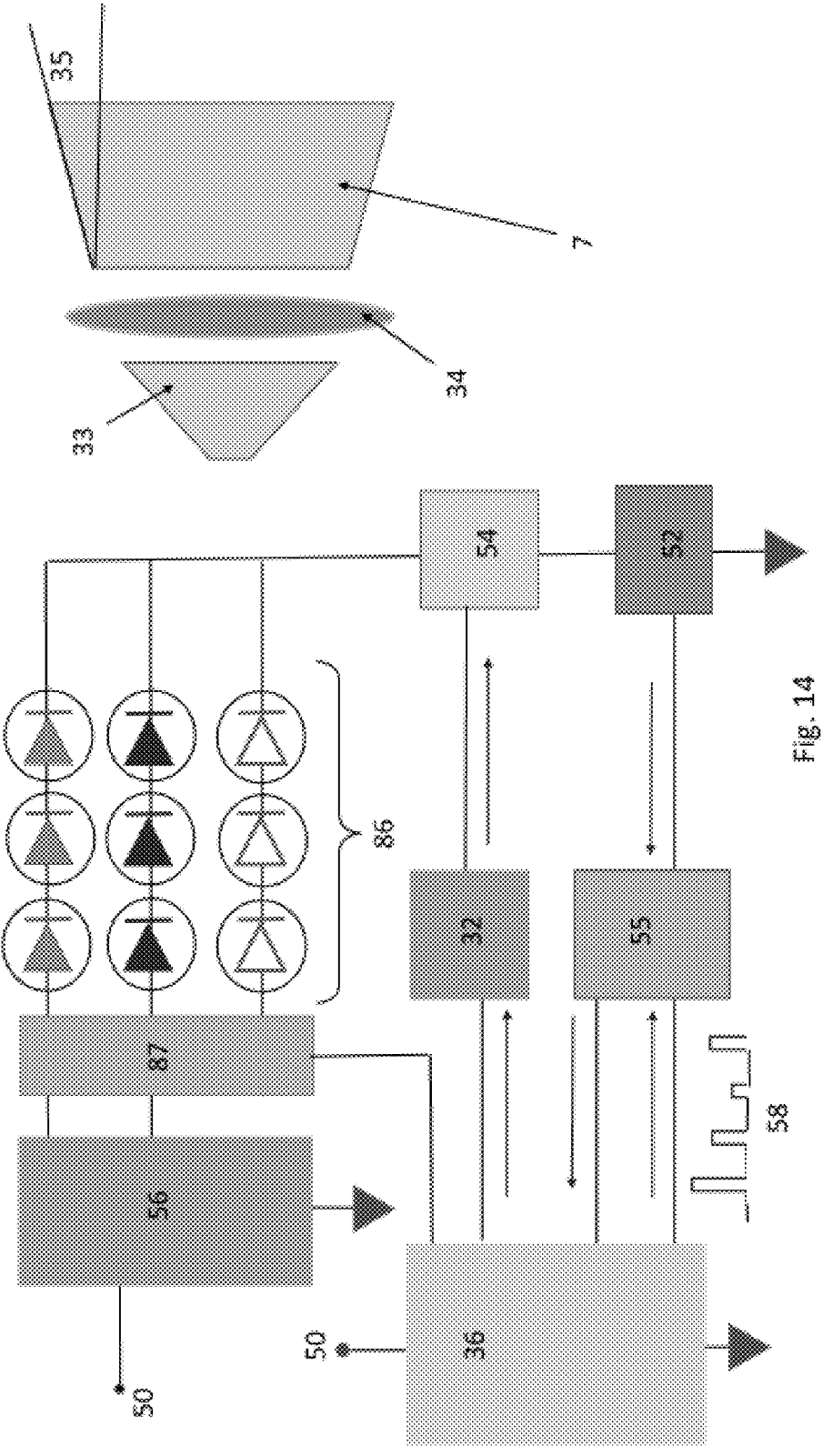
FIG. 14 shows a circuit of a multiband polychromatic emission device using the LED-layered quantum emission system.

Multiple light or photonic heads are assembled using arrays of LEDs or laser diodes with various nominal wavelengths, a basic unit is made up of an array containing light-emitting diodes that cover much of the blue spectrum, the others in the vicinity cover a large part of the red spectrum and others cover the near infrared (between 800 and 950 nanometers). As can be seen in FIG. 14 the low impedance voltage source (56) is connected to a selector of emitters (87) which connects the emitters of the polychromatic matrix (86) based on the wavelength required for each stage of the treatment.

The emission power control (36) selects which will be the light-emitting diodes within the polychromatic matrix (86) that will be activated in each stage of the treatment

What is claimed is:

1. An equipment for destruction of coronaviruses by means of complementary radiation comprising at least one photonic radiation emitter and an ultrasonic pulse emitter assembled in a modular head equipped with mounting and fixing devices, where the photonic radiation emitter is a device of emission comprising an emission head configured to produce light stratified emission by stratified quantum excitation of LEDs to which an OOK-type modulator and an illumination matrix sector selector are integrated, covering the wavelength band from 400 to 460 nanometers, and the photonic radiation emitter is configured to generate photonic pulses through the use of modified light stratified emission, wherein the generated photonic pulses generate mechanical forces by their impact, wherein the light stratified emission is controlled based on a digital signal and the OOK-type modulation.

2. The equipment for destruction of coronaviruses by means of complementary radiation according to claim 1, where the ultrasonic pulse emitter is characterized by being formed by one or more emission elements activated by oscillators modulated in phase and frequency.

3. The equipment for destruction of coronaviruses by means of complementary radiation according to claim 1, comprising one or more pulse-emitting heads of photonic and ultrasonic energy placed in manual or automatic activation supports placed around an element where a patient is placed, where this element can be a bench or a bed, where the bed has at least one surface that is transparent for the radiation of the heads or emitters.

4. The equipment for destruction of coronaviruses by means of complementary radiation according to claim 1, characterized in that it comprises an extracorporeal blood circulation assembly that in turn comprises an irradiation chamber on which photonic and ultrasonic irradiation heads illuminate through a surface transparent to the radiation beams the blood that circulates through the irradiation chamber that later returns to a patient's body.

5. The equipment for destruction of coronaviruses by means of complementary radiation according to claim 1, characterized in that the irradiation heads are connected to a sterilization chamber for medical objects and accessories in such a way that the objects to be sterilized are placed under electromagnetic irradiation beam from a 400 to 460-nanometer head equipped with modulated ultrasonic emission.

6. The equipment for destruction of coronaviruses by means of complementary radiation according to claim 2, comprising one or more pulse-emitting heads of photonic and ultrasonic energy placed in manual or automatic activation supports placed around an element where a patient is placed, where this element can be a bench or a bed, where the bed has at least one surface that is transparent for the radiation of the heads or emitters.

7. The equipment for destruction of coronaviruses by means of complementary radiation according to claim 2, characterized in that it comprises an extracorporeal blood circulation assembly that in turn comprises an irradiation chamber on which photonic and ultrasonic irradiation heads illuminate through a surface transparent to the radiation beams the blood that circulates through the irradiation chamber that later returns to a patient's body.

8. The equipment for destruction of coronaviruses by means of complementary radiation according to claim 2, characterized in that the irradiation heads are connected to a sterilization chamber for medical objects and accessories in such a way that the objects to be sterilized are placed under electromagnetic irradiation beam from a 400 to 460-nanometer head equipped with modulated ultrasonic emission.

9. The equipment for destruction of coronaviruses by means of complementary radiation according to claim 1, wherein the equipment is configured to destroy the coronaviruses, employing wavelength band from 400 to 460 nanometers and ultrasonic and hypersonic mechanical waves, by attacking fat or lipid cover surrounding the coronavirus, thereby leaving core of the coronavirus susceptible to being destroyed.

* * * * *